(12) United States Patent
Ume et al.

(10) Patent No.: US 8,297,122 B2
(45) Date of Patent: *Oct. 30, 2012

(54) METHODS AND SYSTEMS FOR DETECTING DEFECTS IN WELDED STRUCTURES

(75) Inventors: Ifeanyi Charles Ume, Atlanta, GA (US);
Tsun-Yen Wu, Atlanta, GA (US);
Matthew Rogge, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 567 days.

This patent is subject to a terminal disclaimer.

(21) Appl. No.: 12/488,396

(22) Filed: Jun. 19, 2009

(65) Prior Publication Data

US 2010/0319456 A1 Dec. 23, 2010

(51) Int. Cl.
*G01N 29/04* (2006.01)
(52) U.S. Cl. ............................... 73/622; 73/600; 73/602
(58) Field of Classification Search .................... 73/622, 73/598, 600, 627, 602
See application file for complete search history.

(56) References Cited

U.S. PATENT DOCUMENTS

| | | | |
|---|---|---|---|
| 3,436,958 A | 4/1969 | Proctor | |
| 3,575,044 A | 4/1971 | Gibbs et al. | |
| 3,585,851 A | 6/1971 | Walther | |
| 3,693,158 A | 9/1972 | Uthe | |
| 3,791,199 A | 2/1974 | Toth et al. | |
| 4,298,808 A | 11/1981 | Hill | |
| 4,522,064 A | 6/1985 | McMillan | |
| 4,531,409 A | 7/1985 | Koch et al. | |
| 4,869,109 A * | 9/1989 | Miglianico et al. ............. | 73/602 |
| 5,283,418 A | 2/1994 | Bellows et al. | |
| 5,475,613 A | 12/1995 | Itoga et al. | |
| 5,476,010 A | 12/1995 | Fleming et al. | |
| 5,544,256 A | 8/1996 | Brecher et al. | |
| 5,619,998 A * | 4/1997 | Abdel-Malek et al. ....... | 600/437 |
| 5,674,415 A | 10/1997 | Leong et al. | |
| 5,724,138 A * | 3/1998 | Reich et al. ................... | 356/492 |
| 5,764,859 A | 6/1998 | Kim et al. | |
| 5,907,100 A * | 5/1999 | Cook ............................. | 73/602 |
| 5,932,123 A | 8/1999 | Marhofer et al. | |
| 6,125,705 A | 10/2000 | Johnson | |
| 6,335,504 B1 | 1/2002 | Ling et al. | |
| 6,484,584 B2 | 11/2002 | Johnson et al. | |
| 6,497,150 B1 | 12/2002 | Kruzic | |
| 6,532,820 B1 | 3/2003 | Fleming et al. | |
| 6,532,821 B2 * | 3/2003 | Lamouche et al. ............. | 73/643 |
| 6,597,997 B2 | 7/2003 | Tingley | |

(Continued)

OTHER PUBLICATIONS

Signal Separation in Ultrasonic NondestructiveTesting, Matz et al., Acta Polytechnica vol. 47, Jun. 2007.*

(Continued)

*Primary Examiner* — J M Saint Surin
(74) *Attorney, Agent, or Firm* — Dinsmore & Shohl LLP

(57) ABSTRACT

A method for processing ultrasonic response signals collected from a plurality of measurement locations along a weld of a test sample to determine the presence of defects in the weld may include filtering an ultrasonic response signal from each measurement location to produce a plurality of filtered response signals for each measurement location, wherein each filtered response signal corresponds to specific types of defects. Thereafter, a plurality of energy distributions may be calculated for the weld based on the plurality of filtered response signals for each measurement location. The plurality of energy distributions may be compared to corresponding baseline energy distributions to determine the presence of defects in the weld.

19 Claims, 7 Drawing Sheets

U.S. PATENT DOCUMENTS

| | | | |
|---|---|---|---|
| 6,640,632 B1 * | 11/2003 | Hatanaka et al. | 73/598 |
| 6,848,312 B2 | 2/2005 | Georgeson | |
| 6,857,553 B1 | 2/2005 | Hartman et al. | |
| 6,896,171 B2 | 5/2005 | Den Boer et al. | |
| 6,923,067 B2 | 8/2005 | Coen et al. | |
| 6,937,329 B2 | 8/2005 | Esmiller | |
| 6,948,369 B2 | 9/2005 | Fleming et al. | |
| 7,094,989 B2 * | 8/2006 | McJunkin et al. | 219/124.34 |
| 7,132,617 B2 | 11/2006 | Lee et al. | |
| 7,204,147 B2 | 4/2007 | Fujimoto et al. | |
| 7,234,355 B2 | 6/2007 | Dewangan et al. | |
| 7,278,315 B1 | 10/2007 | Klein et al. | |
| 7,516,022 B2 | 4/2009 | Lee et al. | |
| 7,557,558 B2 * | 7/2009 | Barrow | 323/316 |
| 7,728,254 B2 * | 6/2010 | D'Angelo et al. | 219/121.62 |
| 7,784,347 B2 | 8/2010 | Messer et al. | |
| 7,851,753 B2 | 12/2010 | Uto et al. | |
| 7,926,349 B2 | 4/2011 | Sargent | |
| 8,146,429 B2 * | 4/2012 | Ume et al. | 73/622 |
| 2002/0017139 A1 | 2/2002 | Kluft et al. | |
| 2002/0053555 A1 | 5/2002 | Matsuyama | |
| 2003/0167616 A1 | 9/2003 | Harding et al. | |
| 2003/0200809 A1 | 10/2003 | Hatanaka et al. | |
| 2005/0230360 A1 | 10/2005 | Maev et al. | |
| 2007/0038400 A1 | 2/2007 | Lee et al. | |
| 2007/0234809 A1 | 10/2007 | Klein et al. | |
| 2008/0072674 A1 | 3/2008 | Ume et al. | |
| 2008/0210010 A1 | 9/2008 | Orth et al. | |
| 2011/0023609 A1 * | 2/2011 | Ume et al. | 73/600 |
| 2011/0023610 A1 | 2/2011 | Ume et al. | |

OTHER PUBLICATIONS

Amara Graps an Introduction to Wavelets IEEE Computational Science and Engineering, Summer 1995, vol. 2, No. 2, Published by IEEE Computer Society, 10662 Los Vaqueros Circle, Los Alamitos, CA 90720, USA.

Christopher Torrence, Gilbert P. Compo A Practical Guide to Wavelet Analysis Program in Atmospheric and Oceanic Sciences, University of Colorado, Boulder, Colorado Bulletin of the American Meteorological Society, vol. 79, No. 1, Jan. 1998.

Office Action mailed Jan. 11, 2012 as it relates to U.S. Appl. No. 12/534,296.

Notice of Allowance and Allowability mailed Nov. 30, 2011 as it relates to U.S. Appl. No. 12/534,581.

Neural Networks, [Retrieved Aug. 3, 2009] Retrieved from the internet <url:http://learnartificialneuralnetworks.com>.

Back propagation Neural Network, [Retrieved Aug. 3, 2009] Retrieved from the internet <url:http://learnartificialneuralnetworks.com/backpropagation.htm>.

P.K..Simpson Foundations of Neural Networks Proceedings of the Adaptive Control Systems Technology Symposium, Oct. 24-25, 1994, pp. 16-37.

* cited by examiner

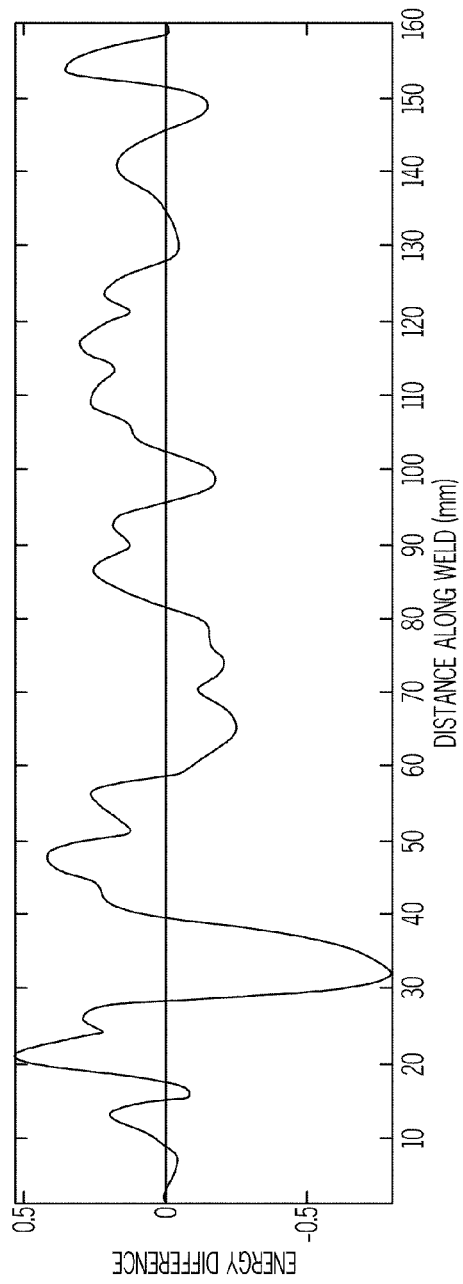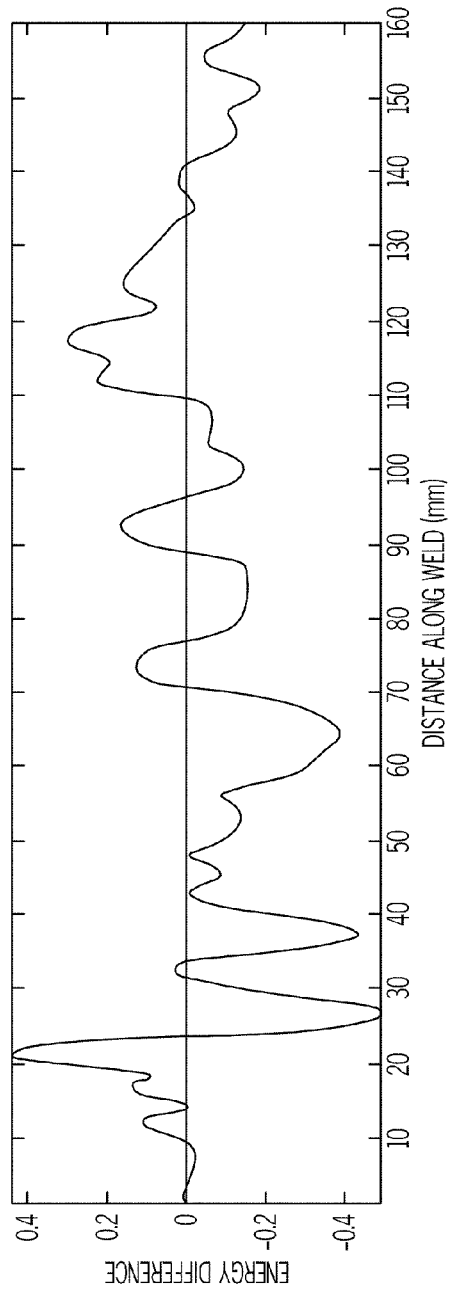

METHODS AND SYSTEMS FOR DETECTING DEFECTS IN WELDED STRUCTURES

CROSS REFERENCE TO RELATED APPLICATIONS

This specification is related to commonly assigned U.S. patent application Ser. No. 12/534,296 filed Aug. 3, 2009 entitled "METHODS AND SYSTEMS FOR DETECTING DEFECTS IN WELDED STRUCTURES UTILIZING PATTERN MATCHING" and U.S. patent application Ser. No. 12/534,581 filed Aug. 3, 2009 entitled "METHODS AND SYSTEMS FOR CLASSIFYING THE TYPE AND SEVERITY OF DEFECTS IN WELDS".

TECHNICAL FIELD

The present specification generally relates to methods and systems for detecting defects in welded structures and, more specifically, to methods for detecting defects in welded structures through ultrasonic inspection and defect detection systems utilizing the same.

BACKGROUND

Various welding techniques are commonly utilized to join metallic parts to produce a wide variety of articles of manufacture such as, for example, automobile components, aircraft components, heavy equipment and machinery. The quality of the weld may play an important role in the structural integrity of the welded structure in which it is employed. However, during the welding or joining operation, defects may be introduced or formed in the weld. Such defects may include blowholes, voids, porosity and insufficient weld penetration depth. Each of these defects may decrease the load bearing capacity of the welded structure. For example, some types of defects may act as stress risers or stress concentrators which may impact the static, dynamic and fatigue strength of the weld and the welded structure. Therefore, it is important to accurately detect and locate potential defects in the welds.

When welds are formed automatically, such as by an automated or robotic welding system, the quality of a weld may be assessed by destructively testing a random sampling of the welded structures that are produced. Destructive tests, such as cut-checks, may be time-consuming and may generate excess product waste. Moreover, automation of such destructive testing methodologies may not be possible.

Efforts have been made to develop various non-destructive testing techniques for detecting defects in welds. However, most of these techniques may not be easily incorporated into manufacturing environments. Moreover, the methodologies employed in such techniques to detect defects may be unable to differentiate between defects and regular features incorporated in the manufactured part.

Accordingly, a need exists for alternative methods and systems for detecting defects in welds in welded structures.

SUMMARY

In one embodiment, a method for processing ultrasonic response signals collected from a plurality of measurement locations along a weld to determine the presence of defects in the weld may include filtering an ultrasonic response signal from each of the measurement locations to produce a plurality of filtered response signals for each of the measurement locations, wherein each filtered response signal corresponds to specific types of defects. Thereafter, a plurality of energy distributions may be calculated for the weld based on the plurality of filtered response signals for each of the measurement locations. Each energy distribution may be compared to a corresponding baseline energy distribution to determine the presence of a defect in the weld.

In another embodiment, a method for testing a weld for the presence of defects may include inducing ultrasonic signals at multiple measurement locations along the weld and collecting an ultrasonic response signal for each of the measurement locations along the weld. The ultrasonic response signals for each of the measurement locations may then be filtered by: decomposing each ultrasonic response signal by discrete wavelet transform with a plurality of mother wavelets to produce sets of wavelet coefficients corresponding to each mother wavelet; band pass filtering the sets of wavelet coefficients to isolate a frequency range sensitive to defects in the weld; and reconstructing each set of filtered wavelet coefficients by inverse discrete wavelet transform to produce a plurality of filtered response signals for each of the measurement locations. A plurality of energy distributions may then be calculated for the weld based on the plurality of filtered response signals for each of the measurement locations along the weld. Each energy distribution may then be compared to a corresponding baseline energy distribution to determine the presence of a defect in the weld.

In yet another embodiment, a defect detection system for determining the presence of defects in a weld may include a controller, an acoustic signal generator, an acoustic signal detector, and a positioning device. The acoustic signal generator, the acoustic signal detector and the positioning device may be electrically coupled to the controller. The controller may be programmed to: induce ultrasonic signals at multiple measurement locations along the weld with the acoustic signal generator; collect an ultrasonic response signal from each of the measurement locations with the acoustic signal detector and store the ultrasonic response signals in a memory operatively associated with the controller; filter the ultrasonic response signal collected from each of the measurement locations to produce a plurality of filtered response signals for each of the measurement locations; calculate a plurality of energy distributions for the weld based on the plurality of filtered response signals for each of the measurement locations; and determine the presence of defects in the weld by comparing each energy distribution to a corresponding baseline energy distribution.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIGS. 8A and 8B are plots representing the energy difference between the energy distribution derived from the ultrasonic response signal of FIG. 6 and a baseline energy distribution for two different mother wavelets.

DETAILED DESCRIPTION

Figure 1:
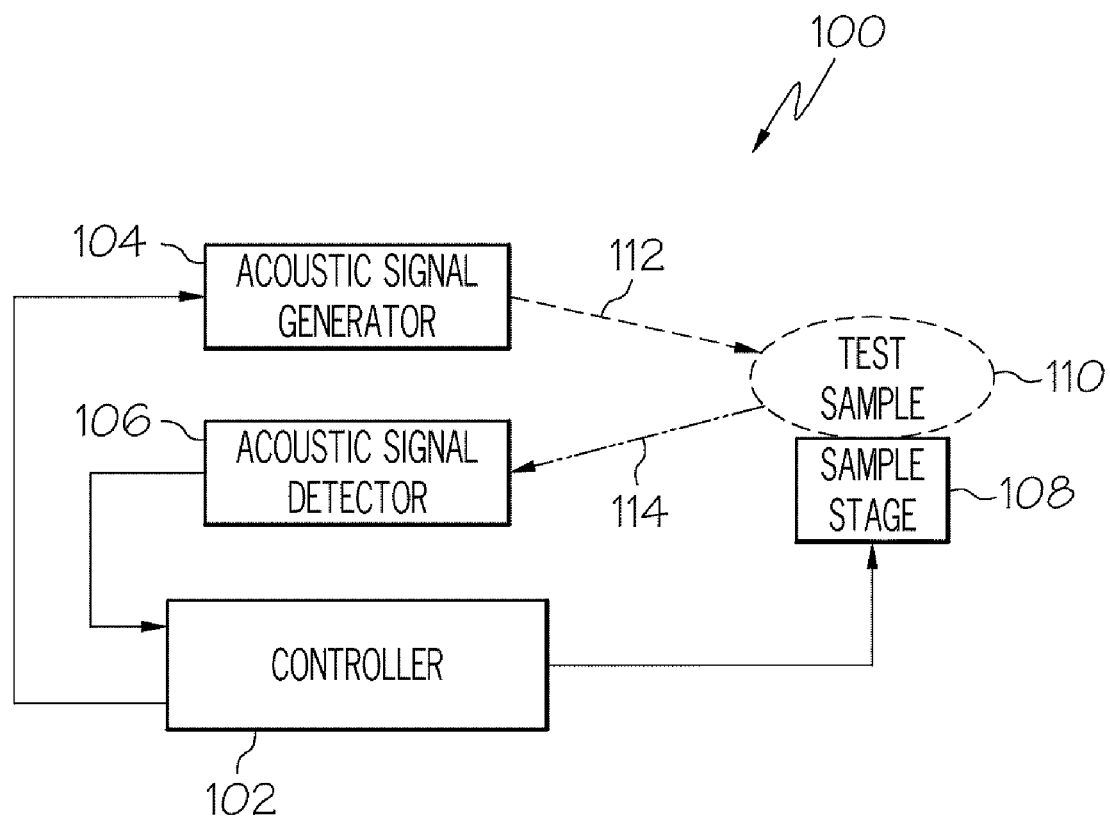
FIG. 1 is a block diagram of a defect detection system according to one or more embodiments shown and described herein.

FIG. 1 generally depicts one embodiment of a defect detection system for determining the presence and location of defects in a weld. The system may generally comprise an acoustic signal generator and an acoustic signal detector coupled to a controller. The various components of the defect detection system and methods of using the defect detection system to determine the presence and location of defects in a welded structure will be described in more detail herein.

Referring now to FIG. 1, a block diagram of a defect detection system 100 is depicted. The defect detection system 100 may generally comprise an acoustic signal generator 104, an acoustic signal detector 106 and a sample stage 108, each of which are electrically coupled to a controller 102. Accordingly, it should be understood that the solid lines and arrows shown in FIG. 1 are generally indicative of the electrical interconnectivity of the various components of the defect detection system 100. It should also be understood that the solid lines and arrows are indicative of electronic signals, such as control signals and/or data signals, propagated between the various components of the defect detection system 100. Further, it should be understood that the dashed line and arrow between the acoustic signal generator 104 and the test sample 110 is indicative of excitation signals 112 transmitted from the acoustic signal generator 104 to a test sample 110 while the dashed line and arrow between the test sample 110 and the acoustic signal detector 106 is indicative of an ultrasonic response signal 114 emitted from the test sample 110 due to the received excitation signal 112 from the acoustic signal generator 104.

In the embodiments shown and described herein, the acoustic signal generator 104 may be a device operable to excite an ultrasonic signal in the test sample 110 without physically contacting the test sample. In one embodiment, the acoustic signal generator 104 may comprise a pulsed laser source operable to excite an ultrasonic signal in the test sample 110 by directing a series of laser pulses onto the surface of the test sample. In another embodiment, the acoustic signal generator 104 may comprise an electromagnetic acoustic transducer (EMAT) operable to excite an ultrasonic signal in the test sample 110 using electromagnetic fields. It should be understood that the acoustic signal generator 104 may comprise other devices suitable for generating ultrasonic signals in the test sample 110.

The acoustic signal detector 106 may generally be a device operable to sense or detect the ultrasonic response signals 114 generated in the test sample 110 without physically contacting the test sample. Accordingly, in one embodiment, the acoustic signal detector 106 may comprise an EMAT sensor operable to detect the acoustic response signal generated in the test sample 110. However, it should be understood that various other non-contact transducers and/or acoustic sensors may be used to detect the ultrasonic response signal 114.

In one embodiment (not shown), where the acoustic signal generator is an EMAT, the EMAT may be used to both excite an ultrasonic signal in the test sample and to detect the ultrasonic response signal from the test sample. Accordingly, it should be understood that a single EMAT may be used as both the acoustic signal generator and the acoustic signal detector.

In the embodiment of the defect detection system 100 shown in FIG. 1, the sample stage 108 may comprise a fixture (not shown) for mounting a test sample to the sample stage. The sample stage 108 may comprise one or more actuators, such as motors and/or stepper motors, mechanically coupled to the stage and electrically coupled to the controller 102. The controller 102, in conjunction with the actuators, may be operable to adjust the position of sample stage 108 and test sample 110 relative to the acoustic signal generator 104 and acoustic signal detector 106 such that the excitation signals 112 emitted by the signal generator may be scanned over the test sample 110 in a controlled manner.

While the embodiments shown and described herein depict the test sample as being fixtured to a moveable sample stage, it should be understood that, in other embodiments (not shown), the acoustic signal generator and the acoustic signal detector may be attached to a moveable stage or similar positioning device electrically coupled to the controller such that the acoustic signal generator and the acoustic signal detector may be adjustably positioned relative to the test sample. Accordingly, it should be understood that the defect detection device may include at least one positioning device for adjusting the relative orientation between the test sample and the acoustic signal generator and acoustic signal detector.

The controller 102 may comprise a computer operable to execute a programmed instruction set and transmit control signals to each of the components of the defect detection system 100. The controller 102 may also be operable to store data received from the acoustic signal detector 106 and analyze the stored data to determine the presence of defects in a weld. Accordingly, it should be understood that the controller 102 may comprise or be coupled to one or more memory devices (not shown) for storing the programmed instruction set and/or data received from the acoustic signal detector. The controller 102 may also be coupled to one or more audible or visual indicators, such as a display (not shown), for providing a user with a visual or audible indication of the presence and location of defects in the test sample and/or an indication of whether the test sample has passed inspection.

Figure 2:
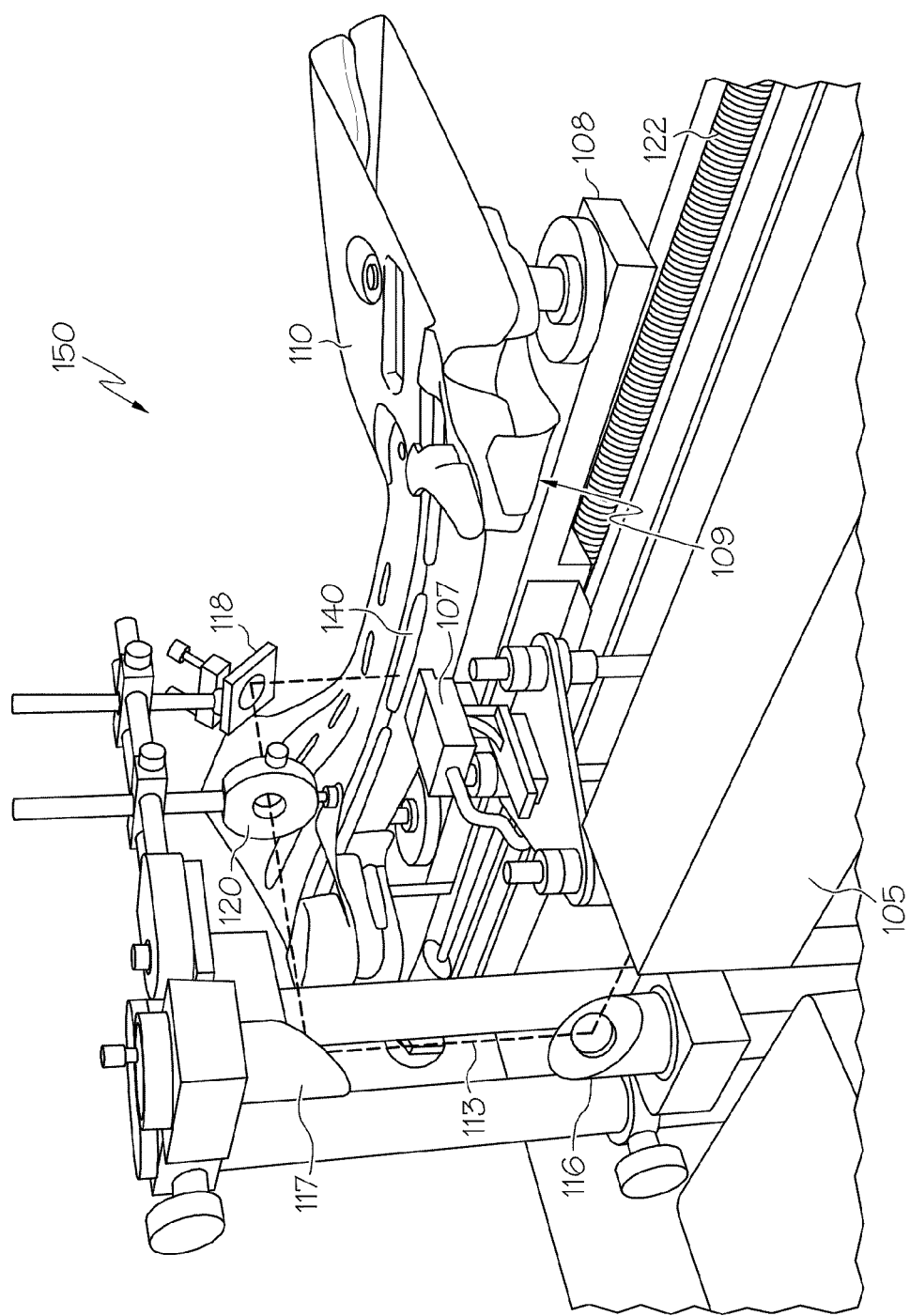
FIG. 2 depicts a defect detection system according to one or more embodiments shown and described herein.

Referring now to FIG. 2, one embodiment of a defect detection system 150 is illustrated. In this embodiment the acoustic signal generator is a pulsed laser source 105, such as an Inlite II-20 Nd:YAG pulsed laser manufactured by Continuum Lasers. The pulsed laser source 105 may have a 20 Hz pulse repetition rate and a pulse width of 10 ns. The spot size of the laser may be about 6 mm and each pulse may have an energy from about 55 mJ to about 450 mJ. The acoustic signal detector may be an EMAT sensor 107. In the embodiment depicted in FIG. 2 the EMAT sensor 107 is manufactured by BWXT Services, Inc. and comprises a four channel broadband receiver having a bandwidth from about 200 kHz to about 2.5 MHz. The EMAT sensor 107 may be coupled to the controller (not shown) with a data acquisition card, such as, for example, a Compuscope 8349 4 channel data acquisition card manufactured by GaGe Applied Technologies which has 14 bit resolution and a data sampling rate of 125 MHz. The sample stage 108 may include one or more fixturing device(s) 109, such as clamps, vices, etc. for holding test sample 110. The fixturing device and/or test sample may include one or more datums (not shown) such that test samples may be positioned on the sample stage with substantially the same orientation relative to the pulsed laser source 105 and the EMAT sensor 107. The sample stage 108 may be mounted to a stepper motor-driven lead screw 122 coupled to the controller such that the position of the sample stage may be adjusted with the controller.

In the embodiment of the defect detection system 150 shown in FIG. 2, the ultrasonic excitation source is the output beam 113 of the pulsed laser source 105 which is optically coupled to the test sample 110 with one or more mirrors. As depicted in FIG. 2, mirrors 116, 117 and 118 form an optical path between the output of the pulsed laser source 105 and the surface of the test sample 110 which directs the output beam 113 onto the surface of the test sample at the desired location. A lens 120 may be disposed in the optical path of the output beam 113 to focus the output beam. Additional optical elements (not shown) may also be inserted in the optical path such as, for example, collimators or other elements which may be used to shape the output beam 113 of the pulsed laser source 105. Further, while the embodiments of the defect detection system 150 shown in FIG. 2 depict the output beam 113 coupled to the test sample 110 with mirrors, it should be understood that the output beam may be directly coupled to the test sample without being first diverted or reflected by a mirror. In alternative embodiments (not shown), the output beam 113 of the pulsed laser source may be coupled to the test sample with one or more optical waveguides, such as an optical fiber or a optical waveguide capable of guiding a laser beam.

As described herein, the pulsed laser source may be used to induce an ultrasonic signal in the test sample. Depending on the energy density or power of the output beam pulse incident on the surface of the test sample, the pulsed-laser source may be utilized to create an ultrasonic signal in either a thermoelastic mode of operation or an ablative mode of operation. For example, the thermoelastic mode of ultrasonic signal generation occurs when the power density of the output beam of the pulsed laser source is relatively low. The output beam rapidly heats a localized area on the surface of the test sample to a temperature less than the melting point of the material due to partial absorption of the laser radiation. The rapid increase in temperature is accompanied by a corresponding expansion of the heated material due to thermoelastic effects. The rapid expansion causes axis-symmetric tensile stresses to develop in the surface of the test sample. When the laser is switched off (e.g., between pulses), the heated region contracts. The expansion and contraction of the top surface of the test sample induces ultrasonic signals that propagate through the test sample.

Alternatively, the ablative mode of ultrasonic signal generation occurs when the power density of the output beam is high enough to heat the surface of the test sample to above the melting temperature of the material. The rapid heating creates axis-symmetric tensile stresses in the surface of the test sample, as described above. However, as the temperature on the surface of the sample exceeds the melting temperature, a small amount of material is vaporized and ejected from the surface of the test sample. Accordingly, in addition to the formation of tensile stresses, a normal reaction force is created against the surface of the sample as the material is ejected. The combination of the normal reaction force and the expansion and contraction of the top surface induces ultrasonic signals that propagate through the test sample. In general, ultrasonic signals generated through the ablative mode are generally stronger that those generated in the thermoelastic mode. In either mode of operation the ultrasonic signals induced in the test sample have frequency content from about 200 kHz to about MHz.

Figure 3:
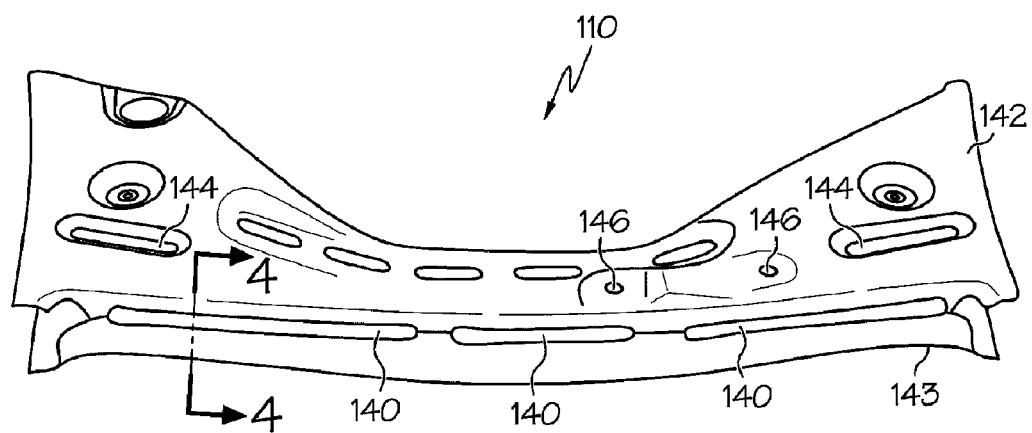
FIG. 3 depicts a test sample comprising a plurality of welds and various manufacturing features.

Referring now to FIGS. 2 and 3, the test sample 110 may generally comprise a metallic structure which comprises at least one weld 140. In the embodiment of the test sample 110 shown in FIGS. 2 and 3, the test sample 110 is a structural support member for an automobile which comprises an upper portion 142 and a lower portion 143, both of which are formed from thin plates of stamped sheet metal. The upper portion 142 may be joined to the lower portion 143 at a lap joint (e.g., the joint shown in FIG. 4) with welds 140. The test sample 110 may also comprise a plurality of manufacturing features including, for example, press marks 144 resulting from a stamping operation and various attachment holes 146 for connecting components to the structural support member.

Figure 4:
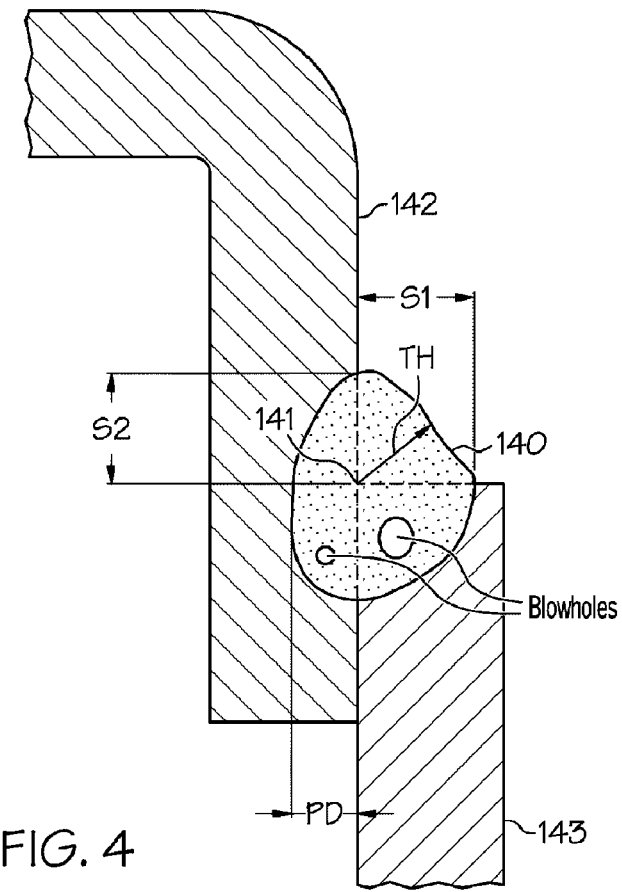
FIG. 4 depicts a cross section of a weld of the test sample of FIG. 3 illustrating various defects that may be present in the weld.
Figure 5:
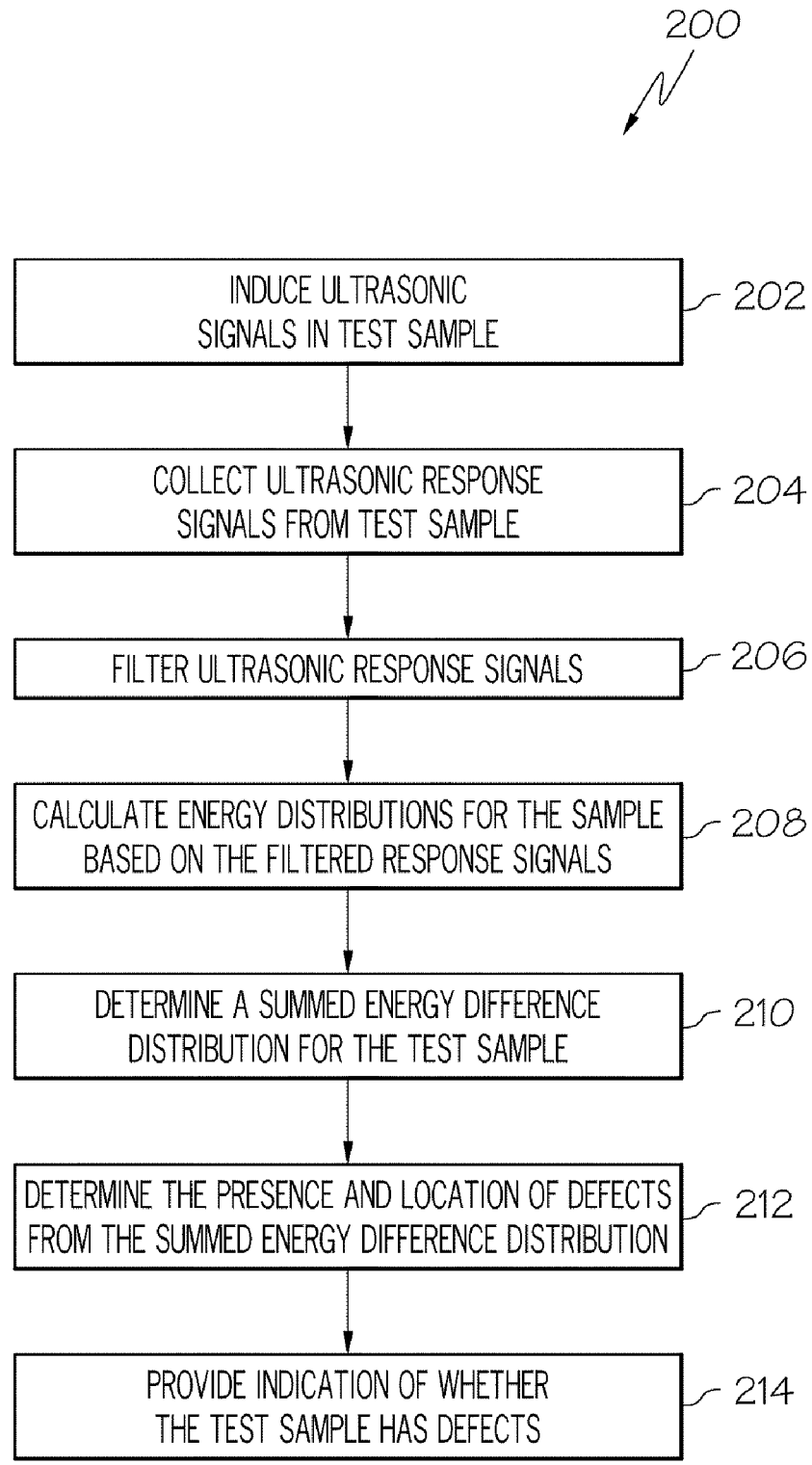
FIG. 5 is a flow diagram of a method for detecting defects in a welded structure according to one or more embodiments shown and described herein.

Referring now to FIG. 4 which depicts a cross section of a lap joint and weld 140 between the upper portions 142 and lower portion 143 of the test sample 110 of FIGS. 2 and 3, the weld 140 may contain one or more different types of defects including, for example, blowholes, insufficient leg length (i.e., short legs), insufficient penetration depth and/or insufficient throat thickness (i.e., short throat). A blowhole defect occurs in the weld when air or gas trapped in the weld escapes from the weld as the weld is formed or as the weld cools. The escaping air or gas leaves a void in the weld and/or forms pores in the weld, both of which may decrease the strength of the weld.

The penetration depth of a weld is defined as the distance PD which the fusion portion of the weld penetrates into the base material, such as, for example, the upper portion 142 of the test sample 110. If the penetration depth is less than a specified percentage of the thickness of the base material an insufficient penetration depth or lack-of-penetration defect occurs. In the embodiments described herein, a lack-of-penetration defect occurs when the distance PD is less than about 30% of the thickness of the upper portion 142 of the test sample. However, it should be understood that the specified percentage may be greater than 30% or less than 30% depending on the application in which the test sample 110 is employed.

The legs of a lap joint weld 140 are defined as the distance between the root 141 of the weld 140 and the toe of the weld (e.g., the point where the weld intersects the base material). The legs of the weld 140 in FIG. 4 are shown as the distances S1 and S2. In the embodiments described herein, a short leg defect is present in the weld if either of the distances S1 or S2 is less than 80% of the material thickness of either the upper portion 142 or lower portion 143 of the test sample 110. However, it should be understood that the specified percentage may be greater than 80% or less than 80% depending on the application in which the test sample 110 is employed.

The throat thickness TH is defined as the shortest distance between the root 141 of the weld 140 and the surface of the weld, as shown in FIG. 4. A short throat defect occurs when the throat thickness of the weld 140 is less than a specified percentage of the thickness of the base material. In the embodiments shown and described herein, a short throat occurs when the throat thickness TH is less than about 70% of the thickness of either the upper portion 142 or lower portion 143 of the test sample. However, it should be understood that the specified percentage may be greater than 70% or less than 70% depending on the application in which the test sample 110 is employed.

Ultrasonic signals induced in the thin plates which comprise the upper portion 142 and the lower portion 143 of the test sample 110 by operating the pulsed laser source in either the thermoelastic mode or ablative mode produce a series of ultrasonic Lamb waves which propagate through the test sample. The Lamb waves may be multi-modal with each mode defined by a set of frequency and wavelength pairs. Due to the different frequencies and wavelengths, each mode of the Lamb wave may react differently to different types of defects encountered in the test sample. For example, for a given type of defect, a first mode defined by a first set of frequency and wavelength pairs may be reflected by the defect while a second mode having a second set of frequency and wavelength pairs may be transmitted through the defect (i.e., the defect does not affect the second mode). Accordingly, different modes of the induced Lamb waves may be sensitive to different types of defects and, by collecting and analyzing an ultrasonic response signal from the test sample, the presence of different types of defects in the test sample may be determined, as will be described in more detail herein.

Referring now to FIG. 2, in order to determine the presence of defects in a weld on a test sample, the test sample 110 may be positioned on the sample stage 108 and attached to the sample stage 108 with one or more fixturing devices 109. The pulsed laser source 105 and EMAT sensor 107 may be positioned such that the EMAT sensor 107 collects an acoustic response signal either transmitted through the weld or reflected by the weld.

For example, in one embodiment, when an acoustic response signal transmitted through the weld is desired, the test sample 110 may be positioned such that the output beam of the pulsed-laser source is incident on one side of the weld 140 and the EMAT sensor 107 is positioned on the other side of the weld 140 and adjacent to the test sample 110, as shown in FIG. 2. Accordingly, it should be understood that the weld 140 is positioned between the point where the output beam 113 of the pulsed laser source 105 contacts the test sample 110 and the EMAT sensor 107. In this embodiment, the ultrasonic signals induced in the test sample 110 and received by the EMAT sensor 107 are transmitted through the weld 140. As defects alter the ultrasonic signal propagating through the weld the ultrasonic signal is transformed to an ultrasonic response signal which is received by the EMAT sensor 107. The ultrasonic response signal carries with it information concerning the presence of defects in the weld 140. Further, the ultrasonic response signal(s) may be correlated to a position along the length of weld 140 and test sample 110 based on the relative positioning between the test sample 110 and the point where the output beam of the pulsed laser source contacts the test sample 110 and/or the position of the EMAT sensor 107.

In another embodiment (not shown), when an acoustic response signal reflected by the weld is desired, the EMAT sensor may be positioned on one side of the weld and the output beam of the pulsed-laser source may be directed onto the test sample on the same side of the weld as the EMAT sensor. The ultrasonic response signal induced in the test sample by the pulsed-laser source propagates through the test sample to the weld which reflects at least a portion of the signal (e.g., the ultrasonic response signal), which is detected by the EMAT sensor. Because portions of the weld which contain defects reflect or transmit the ultrasonic signal differently than portions of the weld without defects, the reflected ultrasonic response signal received by the EMAT sensor carries with it information concerning the presence of defects in the weld.

Referring now to FIGS. 2 and 5-9, one embodiment of a method 200 for detecting the presence of defects in a weld with the defect detection system 150 is depicted. In a first step 202, the controller triggers the pulsed laser source 105 to induce an ultrasonic signal in the test sample 110 by directing a series of beam pulses onto the surface of the test sample, as described above. The controller may be programmed to trigger the pulsed laser source multiple times at each measurement location and the collected ultrasonic response signals generated by each firing of the pulsed laser at each measurement location may be averaged to increase the signal to noise ratio of the collected ultrasonic response signal at that location. In the embodiments described herein the pulsed laser source is operated in an ablative mode to induce ultrasonic response signals in the test sample which have frequency content from about 200 kHz to about 15 MHz. However, it should be understood that the pulsed laser source may also be operated in a thermoelastic mode to generate ultrasonic signals in the test sample. The ultrasonic signal propagates through the test sample 110 and the weld 140 and portions of the ultrasonic signal may be reflected by defects in the weld 140 or other features in the test sample while other portions of the ultrasonic response signal may be transmitted through the weld 140. In this example, the ultrasonic response signal is the signal transmitted or reflected after portions of the ultrasonic signal are reflected and/or defracted by defects and/or other features in the test sample.

In a second step 204, the ultrasonic response signal induced in the test sample 110 is collected with the EMAT sensor 107. In the embodiments described herein, the EMAT sensor 107 is positioned to collect an ultrasonic response signal which is transmitted through the weld 140, as illustrated in FIG. 2 and described above. The EMAT sensor 107 converts the collected ultrasonic response signal to an electrical signal which has a voltage proportional to the amplitude of the ultrasonic response signal. Accordingly, in the embodiments described herein where the collected ultrasonic response signal has been transmitted through the weld 140, electrical signals produced by the EMAT sensor 107 with relatively large voltages correspond to ultrasonic response signals with relatively greater amplitudes while electrical signals with relatively low voltages correspond to ultrasonic response signals with relatively lower amplitudes. The relative magnitude of the ultrasonic response signal may be generally indicative of the absence or presence of defects and/or manufacturing features in the test sample with lower amplitudes indicative of the presence of a defect and/or manufacturing feature and higher amplitudes indicative of the absence of a defect and/or manufacturing feature.

The electrical signal produced by the EMAT sensor 107 is transmitted from the EMAT sensor 107 to the controller (not shown) where the electrical signal is stored in a memory associated with the controller. The amplitude (i.e., the voltage) of the electrical signal is stored in the memory as a function of time and indexed or correlated to a specific position along the weld 140 of the test sample 110. Accordingly, it should be understood that the amplitude of the ultrasonic signal may be a function of both time (t) and position (x) along the weld 140 and, as such, may be written as $f(x,t)$.

After the collected ultrasonic signal is stored in memory for one location along the weld 140, the position of the test sample 110 relative to the pulsed laser source 105 and EMAT sensor 107 may be adjusted such that ultrasonic sonic response signals may be induced and collected from the test sample 110 at a different measurement location along the weld 140. In the embodiment shown in FIG. 2, the position of the test sample 110 relative to the pulsed laser source 105 and EMAT sensor 107 may be adjusted by the controller which sends a control signal to the stepper motor (not shown) coupled to the lead screw 122. Rotation of the stepper motor causes the lead screw 122 to rotate, which, in turn, imparts translational motion to the sample stage 108 thereby adjusting the position of the test sample 110 relative to the pulsed laser source 105 and EMAT sensor 107.

Figure 6:
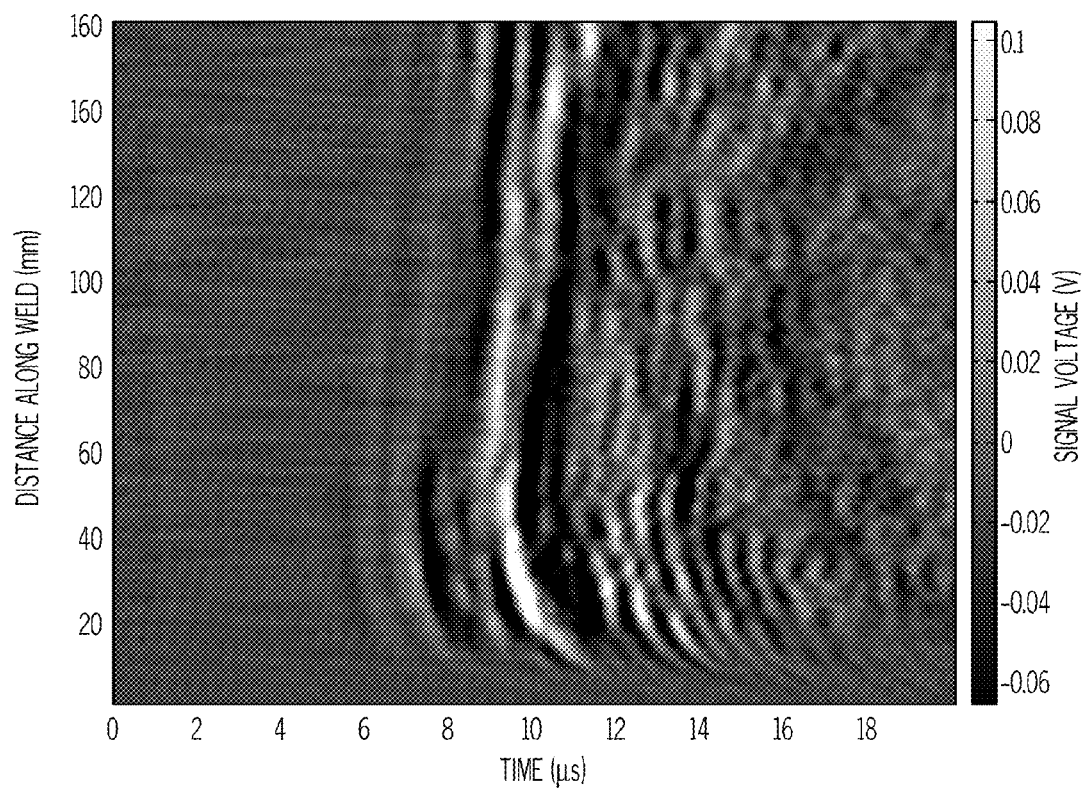
FIG. 6 is a plot of an ultrasonic response signal collected from a test sample according to one or more embodiments shown and described herein.

After the position of the test sample 110 has been adjusted, steps 202 and 204 may be repeated at a new location along the weld 140 and the amplitude of the ultrasonic response signal is stored in the memory operatively associated with the controller as a function of both time (t) and location (x) along the weld. This process of inducing an ultrasonic signal, collecting an ultrasonic response signal and adjusting the position of the test sample may be repeated multiple times to develop a set of ultrasonic response signals for a segment of the weld and/or the entire length of the weld 140. FIG. 6 graphically illustrates a set of ultrasonic response signals collected from one test sample. The y-axis is indicative of the position along the weld, the x-axis is indicative of the time interval over which the ultrasonic response signal was collected, and the gray scale is indicative of the relative amplitude of the collected ultrasonic response signal in units of voltage. In the embodiments shown and described herein, the position of the test sample is adjusted in millimeter increments although larger or smaller increments may be used depending on the desired defect resolution.

Still referring to FIG. 6, the higher frequency/shorter wavelength content of the ultrasonic signals induced in the test sample may be more susceptible to diffraction and/or reflection by features in the test sample than other, lower frequencies. For example, one frequency range particularly susceptible to reflection and/or diffraction by such features may be from about 0.977 MHz to about 1.464 MHz. Accordingly, the corresponding frequencies in the ultrasonic response signal collected from the test sample may contain information regarding the presence of such features. These features may include regular features (i.e., features regularly occurring in each of a plurality test samples) such as manufacturing features (e.g., connector holes, stamp marks, etc.) and irregular features such as defects.

In step 206, the controller may be programmed to filter the ultrasonic response signals collected from the test sample to isolate frequencies most susceptible to reflection and/or diffraction by such features. In the embodiments described herein, the collected ultrasonic response signals for each measurement location (x) along the weld may be filtered into frequency ranges that are sensitive to features (such as defects) in the test sample using discrete wavelet transform (DWT). Specifically, for a specified location x along the weld, the collected ultrasonic response signal f(t) may be decomposed into a set of wavelet coefficients WS(h,k) according to the relationship:

$$WS(h,k) = \int f(t) \Psi_{h,k}^*(t) dt \quad (1)$$

where $\Psi^*_{h,k}(t)$ is the complex conjugate of wavelet $\Psi_{h,k}(t)$. Wavelet $\Psi_{h,k}(t)$ may be a function of a mother wavelet function $\Psi$ which is scaled by scaling parameter $s_0^h$ and shifted by shifting parameter $k\tau_0 s_0^h$ such that:

$$\Psi_{h,k}(t) = \frac{1}{\sqrt{s_0^h}} \Psi\left(\frac{t - k\tau_0 s_0^h}{s_0^h}\right), \quad (2)$$

where t is time and h and k are integers. $s_0$ is generally selected to be 2 and the shifting parameter $\tau_0$ is generally selected to be 1.

Generally, the selection of the mother wavelet $\Psi$ may depend on the shape or form of the collected ultrasonic response signal as a given ultrasonic response signal may be better approximated by a wavelet having a shape or form similar to that of the signal. However, different features present in the test sample may affect the induced ultrasonic signals differently and, as such, it may be difficult to predict the resulting shape of the ultrasonic response signal. Further, different mother wavelets may be sensitive to different features and, as such, certain mother wavelets may be better used to resolve specific types of features. Accordingly, in order to resolve all the various features which may be present in the test sample, a plurality of different mother wavelets j may be used to decompose the ultrasonic response signal for each measurement location. In this approach, $\Psi^j$ denotes a mother wavelet j which has a specific form and feature sensitivity. The mother wavelets used for decomposition of the ultrasonic response signal may be selected from, for example, the Daubechies wavelet family, the Coiflet wavelet family, the Haar wavelet family, the Symmlet wavelet family, the Discrete Meyer (DMEY) wavelet or similar wavelet families and/or combinations thereof. For example, in one embodiment, a total of 24 different mother wavelets (i.e., j=24) may be used to decompose each collected ultrasonic response signal thereby producing 24 different sets of wavelet coefficients. In this embodiment, the 24 mother wavelets may include the DMEY wavelet, wavelets 2-4 from the Coiflet wavelet family, and wavelets 2-20 of the Daubechies wavelet family. However, it should be understood that the number of mother wavelets j used to decompose the collected ultrasonic response signal by DWT may be less than 24 or greater than 24. Further, it should be understood that mother wavelets from a single wavelet family may be used.

After the ultrasonic response signal is decomposed utilizing each of the j mother wavelets, each resulting set of wavelet coefficients may be band-pass filtered to isolate a frequency range most sensitive to defects which, in the embodiments described herein, is from about 0.977 MHz to about 1.464 MHz. Filtering the set of wavelet coefficients is performed by zeroing elements of the set WS(h,k) that correspond to frequency content outside the desired frequency range. In the embodiments described herein, decomposition and filtering by DWT is performed by the controller using Mallet's filter banks algorithm which produces a band-pass filtered set of wavelet coefficients for each mother wavelet at each measurement location along the weld.

After each collected ultrasonic response signal is decomposed with each mother wavelet and filtered, the resulting sets of wavelet coefficients may be reconstructed by inverse discrete wavelet transform (IDWT) to form a filtered response signal $f^j(x,t)$ for each mother wavelet j at each measurement location x along the weld. For example, when 24 mother wavelets are used to decompose and filter the collected ultrasonic response signal(s), and there are 10 separate measurement locations along the weld, 240 filtered response signals are created by IDWT.

In a next step 208, the controller may be programmed to calculate and normalize an energy distribution $E^j(x)$ for each mother wavelet and measurement location based on the filtered response signals $f^j(x,t)$. For example, when 24 mother wavelets are used to decompose the ultrasonic response signals, 24 energy distributions may be calculated. The energy distribution $E^j(x)$ for a mother wavelet j may be calculated and normalized by summing the square of the corresponding filtered response signal $f^j(x,t)$ over the time duration of the signal such that:

$$E^j(x) = \sum_t (f^j(x,t))^2, \quad (3)$$

where, for a particular mother wavelet j, $E^j(x)$ is the energy at location x and $f^j(x,t)$ is the amplitude of the filtered ultrasonic response signal at location x and time t.

Figure 7:
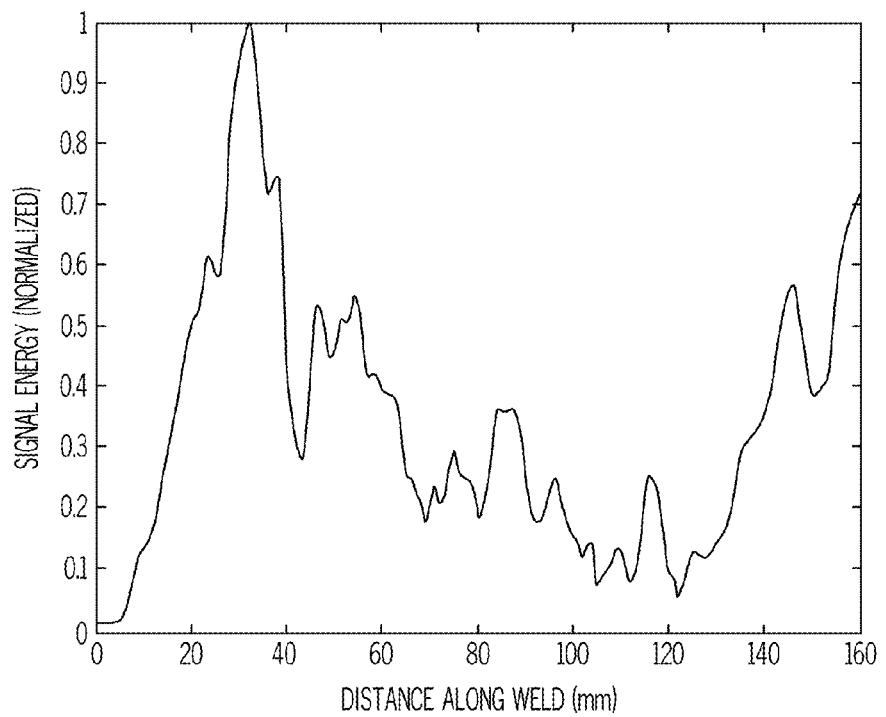
FIG. 7 is a plot of an energy distribution derived from the ultrasonic response signal of FIG. 6 for a particular mother wavelet used to isolate defects sensitive to specific ultrasonic signal frequencies.

The energy distribution $E^j(x)$ for a particular mother wavelet j may be plotted as depicted in FIG. 7 where the x-axis corresponds to the measurement location along the weld and the y-axis corresponds to the normalized signal energy $E^j(x)$ for a particular mother wavelet j. The plotted energy distribution shows that the energy of the ultrasonic response signal fluctuates along the length of the weld. These fluctuations in energy may be caused by the presence of various features in the test sample and/or weld which may reflect or diffract the ultrasonic signal induced in the test sample. Such features may include regular features, such as stamp marks, connector holes, and the like, or irregular features, such as defects and/or changes in the thickness of the weld, as described above.

Accordingly the controller may be programmed to differentiate the regular features (i.e., the features common to all test samples) from the irregular features (i.e., the defects), by comparing the energy distribution for each mother wavelet j to a corresponding average or baseline energy distribution for the same mother wavelet which is indicative of an energy distribution of a weld without any defects. In one embodiment, the baseline energy distribution for a particular mother wavelet j may be determined by averaging corresponding energy distributions for that mother wavelet taken from a plurality of test samples. As the fluctuations in the energy of a single energy distribution due to the presence of irregular features or defects appear as random noise, averaging several energy distributions from different test samples increases the signal to noise ratio in the averaged energy distribution thereby minimizing or mitigating fluctuations in the energy distribution as a result of irregular features or defects. In this embodiment, the baseline energy distribution $E_{baseline}^j(x)$ may be determined by the equation:

$$E_{baseline}^j(x) = \frac{\sum_i E_i^j(x)}{N}, \quad (4)$$

where N is the total number of test samples used to determine the baseline energy distribution, i is an integer from 1 to N, and is indicative of the identity of a particular test sample, and $E_i^j(x)$ is the energy distribution for test sample i for a particular mother wavelet j.

In the embodiments where the baseline energy distributions $E_{baseline}^j(x)$ are calculated by averaging corresponding energy distributions from a plurality of different test samples, the controller may be pre-programmed with the baseline energy distributions. Thereafter, as the defect detection system analyzes additional test samples for the presence of defects, the controller may be programmed to continuously update each baseline energy distribution with energy distributions from each additional test sample that is analyzed thereby further refining the baseline energy distributions. Alternatively, the baseline energy distributions $E_{baseline}^j(x)$ may be pre-programmed into the controller and remain constant for all test samples analyzed by the defect detection system.

Because the baseline energy distribution for each mother wavelet j is essentially free from the influence of irregular features or defects in the weld, the presence of defects in the weld may be determined by comparing the baseline energy distribution for a particular mother wavelet j to a corresponding energy distribution for a test sample. When the energy at a particular location is lower than the average energy at the same location, it is likely that the weld contains some type of defect (e.g., short leg, short throat, blow hole, etc.) at the weld location.

For example, FIGS. 8A and 8B graphically depict the energy difference between an energy distribution and a baseline energy distribution for two different mother wavelets on ultrasonic response signals collected from the same test sample. In both cases, the energy difference ED was calculated by subtracting the baseline energy distribution from the energy distribution for each mother wavelet (e.g., $ED = E^j(x) - E_{baseline}^j(x)$). FIG. 8A shows the energy difference between an energy distribution calculated by decomposing the collected ultrasonic response signal with a Daubechies 2 mother wavelet and subtracting the baseline energy distribution for the corresponding mother wavelet. FIG. 8B shows the energy difference between an energy distribution calculated by decomposing the collected ultrasonic response signal with a Daubechies 3 mother wavelet and subtracting the baseline energy distribution for the corresponding mother wavelet. In both FIGS. 8A and 8B, locations along the weld which have an energy difference of less than zero are indicative of the potential presence of a defect at that location. FIG. 8A indicates that defects may be present in the weld from 5-8 mm, 16-17 mm, 29-39 mm, 59-81 mm, 96-102 mm, 129-135 mm and 146-151 mm. FIG. 8B indicates that defects may be present in the weld from 5-9 mm, 24-31 mm, 34-70 mm, 77-88 mm, 97-109 mm, and 141-160 mm.

While FIGS. 8A and 8B indicate the potential presence of defects in the weld, FIGS. 8A and 8B also graphically illustrate that ultrasonic signals decomposed and filtered with different mother wavelets may be sensitive to different types of defects which may be present in the weld. Accordingly, in a next step 210, a summed energy difference is determined for the sample in order to more fully analyze a weld for the presence of defects. The summed energy difference (SED) for a given test sample i is the difference between the energy distribution for a particular mother wavelet and the corresponding baseline energy distribution for the same mother wavelet summed over all mother wavelets j and thus incorporates the energy distributions for all the mother wavelets and their corresponding defect sensitivities into a single expression. Specifically, the SED may be written as:

$$SED_i(x) = \sum_j (E_i^j(x) - E_{baseline}^j(x)), \quad (5)$$

where $E_i^j(x)$ is the energy distribution of a test sample i for a mother wavelet j, $E_{baseline}^j(x)$ is the baseline energy distribution for the corresponding mother wavelet and j is an integer greater than or equal to zero, and, in the examples described herein, is from 1-24.

Figure 9:
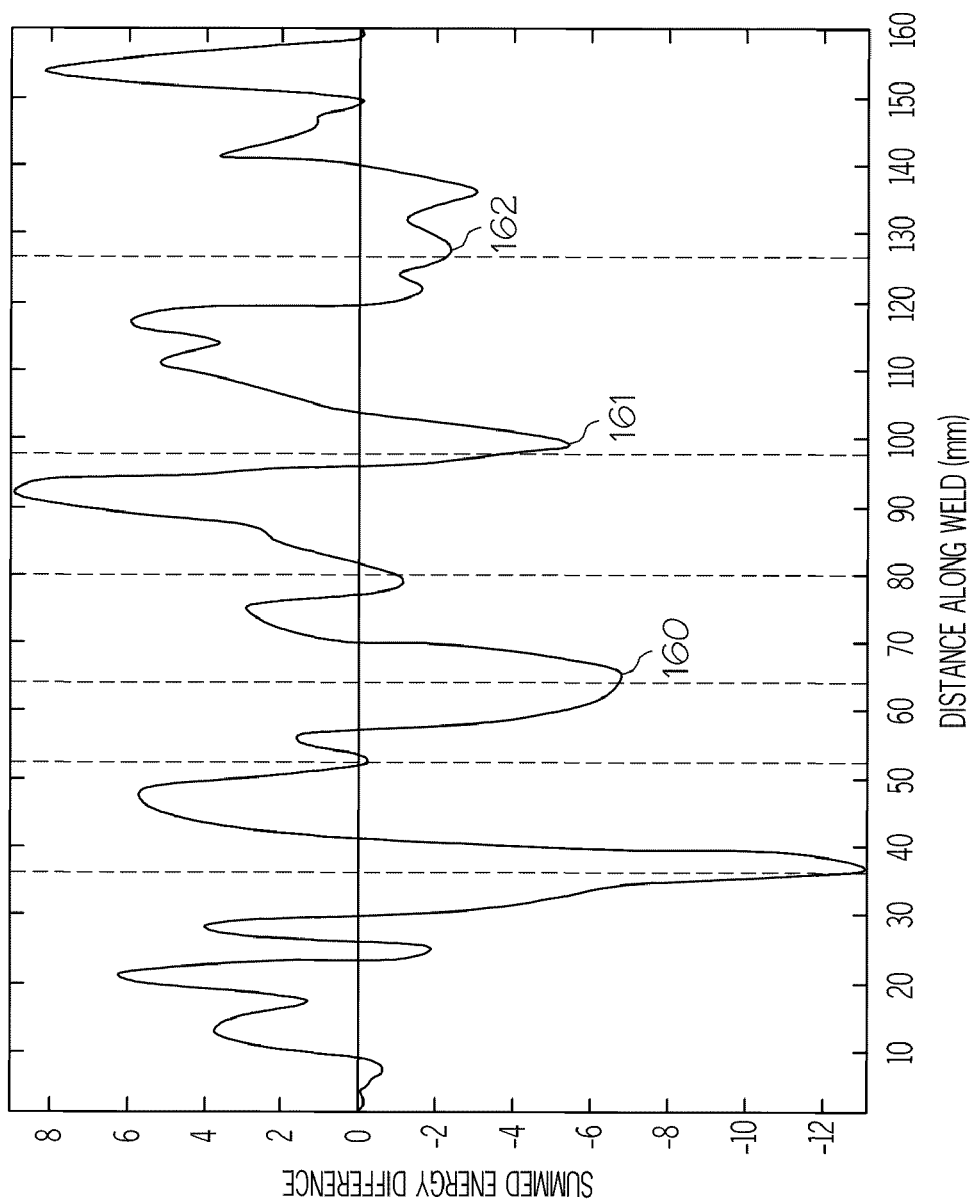
FIG. 9 is a plot of a Summed Energy Difference distribution according to one embodiment shown and described herein.

Referring now to FIG. 9, the SED for a particular sample is graphically depicted. As with the energy differences depicted in FIGS. 8A and 8B, locations which have a summed energy value less than zero are potential defect locations. For example, in FIG. 9, locations at 25 mm, 30-40 mm, 58-70 mm, 78-81 mm, 98-103 mm and 121-140 mm have summed energy distributions below zero which indicates that the energy at these locations is below the average energy distribution for the sample at that location.

When the Summed Energy Difference distribution is below a specified low energy threshold (which is −0.5 in the present example) the location is identified by the controller as the location of a defect. For example, in the SED shown in FIG. 9, locations 160, 161 and 162 are defect locations as these locations have an SED of less than −0.5. In the embodiments described herein, the low energy threshold is experimentally determined by destructively testing test samples after the test samples have been analyzed with the defect detection system. The results of the defect detection system are correlated to the destructive testing results and, utilizing the defect criteria discussed above, the low energy threshold is established. Accordingly, while the embodiments described herein utilize −0.5 as a low energy threshold, it will be understood that the low energy threshold may be less than or greater than −0.5 depending on the specific defect criteria utilized.

In a next step 212, the controller may be programmed to analyze the summed energy distribution and, when the summed energy location for a particular location is less than the low energy threshold, the controller designates the location as containing a defect and stores this designation in memory.

In a next step 214, the controller may be programmed to provide a user with an indication of whether the test sample has passed or failed inspection based on the presence of defects in the sample. For example, when the test sample contains defects, the controller may provide the user with an audible and/or visual indication that the test sample has failed inspection with an indicator coupled to the controller. Alternatively or additionally the controller may display a message to the user on an attached monitor which indicates that the part has failed inspection and identifies the location of the detected defects such as by displaying a plot similar to that shown in FIG. 9. Similar procedures may be used to indicate to the user that the test sample does not contain defects and has passed inspection.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for processing ultrasonic response signals collected from a plurality of measurement locations along a weld to determine the presence of a defect in the weld, the method comprising:
  filtering an ultrasonic response signal from each of the measurement locations to produce a plurality of filtered response signals for each of the measurement locations, wherein each filtered response signal corresponds to specific types of defects;
  calculating a plurality of energy distributions for the weld based on the plurality of filtered response signals for each of the measurement locations; and
  comparing each energy distribution to a corresponding baseline energy distribution to determine the presence of a defect in the weld.

2. The method of claim 1 wherein the ultrasonic response signal is filtered by:
  decomposing the ultrasonic response signal from each of the measurement locations by discrete wavelet transform with a plurality of mother wavelets to produce sets of wavelet coefficients corresponding to each of the mother wavelets;
  band pass filtering the sets of wavelet coefficients to isolate a frequency range of the ultrasonic response signal sensitive to defects in the weld; and
  reconstructing each set of filtered wavelet coefficients by inverse discrete wavelet transform to produce the plurality of filtered response signals.

3. The method of claim 1 wherein each energy distributions is compared to the corresponding baseline energy distribution by calculating a summed energy difference distribution for the weld.

4. The method of claim 1 further comprising determining the baseline energy distribution by averaging corresponding energy distributions from a plurality of test samples.

5. A method for testing a weld for the presence of defects, the method comprising:
  inducing ultrasonic signals at multiple measurement locations along the weld;
  collecting an ultrasonic response signal for each of the measurement locations along the weld;
  filtering the ultrasonic response signal from each of the measurement locations by:
    decomposing the ultrasonic response signal by discrete wavelet transform with a plurality of mother wavelets to produce sets of wavelet coefficients corresponding to each mother wavelet;
    band pass filtering the sets of wavelet coefficients to isolate a frequency range sensitive to defects in the weld;
    reconstructing each set of filtered wavelet coefficients by inverse discrete wavelet transform to produce a plurality of filtered response signals for each measurement location;
  calculating a plurality of energy distributions for the weld based on the plurality of filtered response signals for each of the measurement locations; and
  comparing each of the plurality of energy distributions to a corresponding baseline energy distribution to determine the presence of a defect in the weld.

6. The method of claim 5 wherein each energy distributions is compared to the corresponding baseline energy distribution by calculating a summed energy difference distribution for the weld.

7. The method of claim 5 further comprising determining the baseline energy distribution by averaging corresponding energy distributions from a plurality of test samples.

8. The method of claim 5 wherein the ultrasonic response signal for each measurement location is filtered to isolate a frequency range from about 0.977 MHz to about 1.464 MHz.

9. The method of claim 5 wherein the induced ultrasonic signals have a frequency content from about 200 kHz to about 15 MHz.

10. The method of claim 5 wherein ultrasonic signals are induced by directing an output beam of a pulsed laser source on to a surface of a test sample in which the weld is located.

11. The method of claim 10 wherein the pulsed laser source is operated in an ablative mode of operation.

12. The method of claim 5 wherein:
 a plurality of ultrasonic signals are induced in the weld at each of the measurement locations; and
 a plurality of ultrasonic response signals are collected at each of the measurement locations and averaged.

13. A defect detection system for determining the presence of defects in a weld, the defect detection system comprising a controller, an acoustic signal generator, an acoustic signal detector, and a positioning device, wherein the acoustic signal generator, the acoustic signal detector and the positioning device are electrically coupled to the controller and the controller is programmed to:
 induce ultrasonic signals at multiple measurement locations along the weld with the acoustic signal generator;
 collect an ultrasonic response signal from each of the measurement locations with the acoustic signal detector and store the ultrasonic response signals in a memory operatively associated with the controller;
 filter the ultrasonic response signal collected from each of the measurement locations to produce a plurality of filtered response signals for each of the measurement locations;
 calculate a plurality of energy distributions for the weld based on the plurality of filtered response signals for each of the measurement locations; and
 determine the presence of defects in the weld by comparing each energy distribution to a corresponding baseline energy distribution by calculating a summed energy difference distribution for the weld and identifying locations along the weld which have a summed energy difference that is less than a low energy threshold.

14. The defect detection system of claim 13 wherein the acoustic signal generator is a pulsed laser source.

15. The defect detection system of claim 13 wherein the acoustic signal detector is an EMAT sensor.

16. The defect detection system of claim 13 wherein the controller is programmed to filter the ultrasonic response signal by:
 decomposing the ultrasonic response signal by discrete wavelet transform with a plurality of mother wavelets to produce sets of wavelet coefficients corresponding to each mother wavelet;
 band pass filtering the sets of wavelet coefficients to isolate a frequency range of the ultrasonic response signal sensitive to defects in the weld; and
 reconstructing each set of filtered wavelet coefficients by inverse discrete wavelet transform to produce the plurality of filtered response signals.

17. The defect detection system of claim 13 wherein:
 the defect detection system further comprises an indicator coupled to the controller; and
 the controller is programmed to provide an indication with the indicator that the weld contains defects or is free from defects.

18. The defect detection system of claim 13 wherein the indicator is a display coupled to the controller and the controller is programmed to indicate the presence and location of defects identified in the weld on the display.

19. A method for processing ultrasonic response signals collected from a plurality of measurement locations along a weld to determine the presence of a defect in the weld, the method comprising:
 filtering an ultrasonic response signal from each of the measurement locations to produce a plurality of filtered response signals for each of the measurement locations, wherein each filtered response signal corresponds to specific types of defects;
 calculating a plurality of energy distributions for the weld based on the plurality of filtered response signals for each of the measurement locations; and
 determining the presence of defects in the weld by comparing each energy distribution to a corresponding baseline energy distribution by calculating a summed energy difference distribution for the weld and identifying locations along the weld which have a summed energy difference that is less than a low energy threshold.

* * * * *